United States Patent [19]

Igarashi et al.

[11] 4,088,778

[45] May 9, 1978

[54] METHOD FOR THE TREATMENT OF HYPERTENSION

[75] Inventors: Toshiji Igarashi, Tokorozawa; Shinzaburo Ohtake, Tokyo, both of Japan

[73] Assignee: Eisai Co., Ltd., Tokyo, Japan

[21] Appl. No.: 671,931

[22] Filed: Mar. 30, 1976

[30] Foreign Application Priority Data

Apr. 2, 1975 Japan .................................. 50-39206

[51] Int. Cl.² .......................................... A61K 31/355
[52] U.S. Cl. .................................................... 424/284
[58] Field of Search ........................................ 424/284

[56] References Cited

U.S. PATENT DOCUMENTS 3,071,512  1/1963  Feldman .............................. 424/284

OTHER PUBLICATIONS

Merck Index, Eighth Edition, (1968), pp. 1056, 1114–1115.
Derwent Abstract of Offenlegungsschrift 2, 144,249, Mar. 9, 1972.
Allardyce et al., Chemical Abstracts, 45:3939c.
Naito et al., Chemical Abstracts, 84:1915y, 1/5/76.

*Primary Examiner*—Stanley J. Friedman
*Attorney, Agent, or Firm*—Blanchard, Flynn, Thiel, Boutell & Tanis

[57] ABSTRACT

Hypertension is therapeutically treated by the administration of a vitamin E derivative to a hypertensive.

5 Claims, 3 Drawing Figures

METHOD FOR THE TREATMENT OF HYPERTENSION

BACKGROUND OF INVENTION

1. Field of Invention

The present invention relates to a method for the treatment of hypertension comprising administering a therapeutically effective amount of a vitamin E derivative to a hypertensive.

2. Description of Prior Arts

Hypertension is a common geriatric disease. With the recent increase of the number of the aged, the number of patients having hypertension is increasing. Accordingly, the treatment of hypertension is a very important problem, but since a great variety of factors are considered as causes of hypertension, no decisive method has been developed.

As known antihypertensive agents, there can be mentioned Reserpine type drugs, Adrenergic blocking agents, Diuretic and hypotensive agents such as hydrochlorothiazide, hydralazine drugs and Dopa decarboxylase inhibitors. Each of these antihypertensive agents has various troublesome side effects, such as described below.

(1) Reserpine, one of the rauwolfia alkaloids, is an antihypertensive agent which has been used for a long time, but it produces undesirable side effects caused by inhibition of the central nervous system, such as asthenic feeling.

(2) Adrenergic blocking agents represented by phenoxybenzamine produce such undesirable side effects as orthostatic hypotensive asthenia and tachycardia.

(3) Diuretic and hypotensive agents such as hydrochlorothiazide have a moderate hypotensive activity and are used for the treatment of hypertension, but if they are administered for a long time, such undesirable side effects as hypokalemia, hypercirycemia and manifestation of latent diabetes are produced.

(4) Hydralazine has a high hypotensive activity, but because of the function mechanism of this agent, it increases the amount of blood fed to the heart and the pulse frequency and thus increases the load on the heart. Accordingly, it cannot be administered to patients having cardiac insufficiency and coronary insufficiency. Further, as frequently occurring, undesirable side effects, there are mentioned multiple arthritis resembling rheumatic arthritis and lupus erythematosus.

(5) Dopa decarboxylase inhibitors represented by $l$-$\alpha$-Methyl Dopa have a high hypotensive activity, but when they are administered for a long time, such undesirable side effects as mammary hypertrophy, paraesthesia, nightmare and Parkisonism are produced.

As is apparent from the foregoing considerations, the known antihypertensive agents are insufficient with respect to the durability of the hypotensive effect and reduction of side effects. Accordingly, development of antihypertensive agents having a higher activity and a higher safety has been desired in the art.

SUMMARY OF INVENTION

In view of the foregoing state of the art, the present inventors made animal experiments on various chemicals and agents, and they have found that vitamin E derivatives are very effective. They have made the further research works and found that when vitamin E derivatives are administered to hypertensives, they exhibit a moderate, but durable, hypotensive effect and improve subjective symptoms of hypertension such as the stiffness in the shoulders and the heaviness in the head, while manifestation of side effects is greatly inhibited.

The term "vitamin E derivative" referred to in the present invention mainly means esters of vitamin E. As the vitamin E ester, there can be mentioned, for example, a nicotinic acid ester of vitamin E, an acetic acid ester of vitamin E and a succinic acid ester of vitamin E.

It is a primary object of the present invention to provide a novel method for the treatment of hypertension.

It is another object of the present invention to provide a novel medicine for the treatment of hypertension.

Still another object of the present invention is to provide a hypotensive agent which produces much reduced side effects and can be administered continuously for a long time.

One of the nicotinic acid esters of vitamin E to be used in the present invention, namely $dl$-$\alpha$-tocopheryl nicotinate (hereinafter referred to as "TN"), is a yellow waxy substance having a melting point of 35° to 40° C. and it is easily soluble in acetone, benzene, chloroform, ether and ethanol, but is hardly soluble in water.

TN may be prepared according to a customary esterification method.

More specifically, $dl$-$\alpha$-tocopherol is reacted with a reactive derivative of nicotinic acid such as nicotinic anhydride or nicotinic chloride in the presence of a hydrochloride and pyridine, and the resulting reaction product is post-treated and purified by column chromatography, whereby pure $dl$-$\alpha$-tocopheryl nicotinate is obtained.

One of the acetic acid esters of vitamin E, namely $dl$-$\alpha$-tocopheryl acetate (hereinafter referred to as "TA"), is a colorless or yellow transparent viscous liquid, and it is soluble in acetone, ether, chloroform and ethanol but is hardly soluble in water. TA is generally prepared according to a customary esterification method.

The dosage of the agent of the present invention is varied depending on the kind of hypertension and the disease condition, but it is generally administered in an amount of about 50 to about 1200 mg per day.

The hypotensive agent of the present invention may be administered in any of the forms of powder, tablet, capsule, injection and the like.

When the hypotensive agent is administered in the form of a powder, it is used in the state of being adsorbed on an inorganic excipient such as magnesium carbonate, silicic anhydride [Siloid and Carplex (trademarks)], synthetic aluminum silicate and calcium phosphate or an organic excipient such as lactose, corn starch and cellulose [Avicel (trademark)]. When the agent is administered in the form of tablets or capsules, the so prepared powder is formed into tablets or capsules according to customary methods.

When the agent is administered in the injection dosage form, according to the conventional technique, it is water-solubilized by using a non-ionic surface active agent and is formed into an injectable liquid. As the non-ionic surface active agent, there can be mentioned, for example, hydrogenated castor oilethylene oxide adduct [for example, Nikkol HCO (trademark) and Emalex HC (trademark)], sorbitan fatty acid ester-ethylene oxide adduct [for example, Tween (trademark)], alkyl phenolethylene oxide adduct, fatty acid-ethylene oxide adduct, and sorbitan fatty acid ester [for example, Span (trademark)]. When the agent is used in the injection form, conventional adjuvants such as propylene glycol and glucose may be added without any particular disadvantage.

Figure 1:
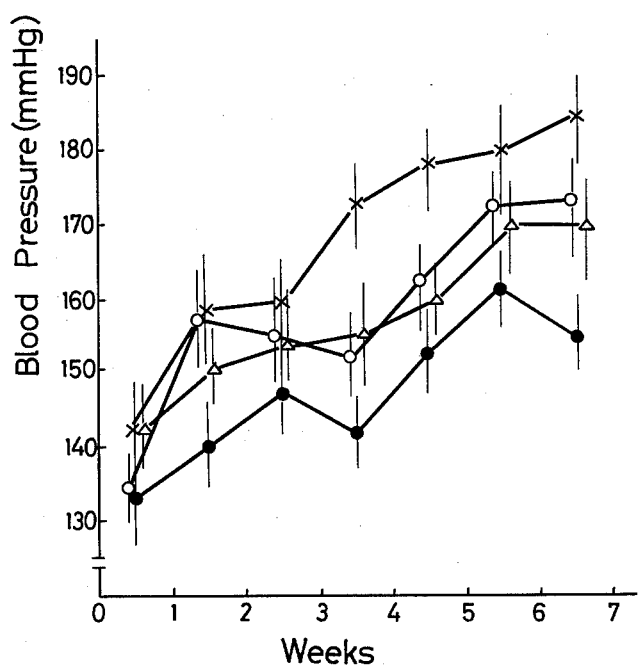
FIG. 1 illustrates influences of TN on hypertension in rats caused by DOCA.

In these drawings, the mark "x" shows the case of control; "o", the case of 20 mg/kg of TN; "•", the case of 100 mg/kg of TN; and "Δ", the case of 88 mg/kg of TA.

Toxicities of TN and TA will now be described.

(A) Acute Toxicity:

According to the conventional method, the acute toxicity was tested on mice and rats to obtain results shown in Table 1.

From the results shown in Table 1, it will readily be understood that no test animal was killed even in the case of massive administration (administration of the maximum amount that can be administered), and that TN and TA have a very high safety.

Table 1

|  | Route | Sex | $LD_{50}$(mg/Kg) |
|---|---|---|---|
| Rats | P.O. | M | > 15000 |
|  |  | F | > 15000 |
|  | S.C | M | > 15000 |
|  |  | F | > 15000 |
|  | I.M. | M | > 10000 |
|  |  | F | > 10000 |
|  | I.P | M | > 2000 |
|  | I.V | M | > 250 |
|  |  | F | > 250 |
| Mice | P.O | M | > 20000 |
|  |  | F | > 20000 |
|  | S.C | M | > 20000 |
|  |  | F | > 20000 |
|  | I.M | M | > 15000 |
|  |  | F | > 15000 |
|  | I.P | M | > 4000 |
|  | I.V | M | > 1000 |
|  |  | F | > 1000 |

M: Male    F: Female (B) Subacute and Chronic Toxicities:

TN and TA were separately administered to rats and beagles at daily doses of 100 to 1000 mg/Kg and 100 mg/Kg, respectively, continuously for 3 or 6 months. There were no deaths, and inhibition of the body weight was not observed. In haematological and haemetobiological surveys and histological surveys of main organs such as liver, kidney, heart, lung, stomach, adrenal and spermary, no manifestation of the toxicity was observed.

(C) Teratogenetic Property Test:

Even when TN and TA were separately administered orally to pregnant mice or pregnant rats at dosages of 100 to 1200 mg/Kg, no influences were observed on mother animals, embryos and newborn babies. Thus, it was confirmed that TN and TA have no teratogenetic property.

The effects of the present invention will now be described by reference to some examples of pharmacological tests.

(A) Hypotensive effect on experimental hypertension caused by administration of desoxycorticosterone (hereinafter referred to as "DOCA"):

Right kidneys were removed from 6-week-old male wistar rats, and a 1% aqueous solution of sodium chloride was given as drinking water and 12.5 mg/Kg of DOCA was intramuscularly injected every week. The change of the blood pressure was examined over a period of 6 weeks.

48 rats, each having one kidney removed, were divided into 6 groups, each consisting of 8 rats, and each group was placed in a cage. With respect to each group, a gum arabic solution was administered to 2 rats as non-administered control animals. 20 mg/Kg of TN was administered once a day to each of two rats among the remaining 6 rats, and 100 mg/Kg of TN was administered once a day to each of two rats among the remaining 4 rats. 88 mg/Kg of TA was administered once a day to each of the remaining two rats. TN and TA were administered in the form of a suspension in gum arabic. The blood pressure was measured by a Shimazu type systolic pressure continuous recording apparatus detecting pulse waves of rats taken in a thermostat fixed box maintained at 30° C.

Results are shown in FIG. 1.

As is apparent from the results shown in FIG. 1, the gradient of increase of the blood pressure was lower in the administered groups than in the control group. The effect was especially conspicuous in the group to which 100 mg/Kg of TN had been administered. The blood pressure was 150 to 170 mm Hg on the average. The numbers of individual rats in which the blood pressure was elevated to 170 mm Hg or higher were 9 among 11 rats in the Control (non-administered) group, 5 among 10 rats in the 20 mg/Kg TN administered group, 3 among 12 rats in the 100 mg/Kg TN administered group, and 4 among 12 rats in the 88 mg/Kg TA administered group.

(B) Hypotensive Effect on Rats of Spontaneous Hypertension:

Experiments were conducted by using two classes of rats of spontaneous hypertension (hereinafter referred to as "SHR"; provided by Nippon Rat K.K.) differing in the age. In the first experiment, 9-month-old chronic hypotensive SHR (hereinafter referred to as "old SHR"), and in the second experiment, 7-week-old SHR in which hypertension was advancing (hereinafter referred to as "young SHR") was used.

(1) Experiment on Old SHR:

40 of 9-month-old male SHR (having a body weight of 360 to 450 g) were divided into 10 groups, each consisting of 4 rats, and each group was placed in a cage. One of the rats in each cage was used as the non-administered control animal, and 20 mg/Kg of TN, 100 mg/Kg of TN and 88 mg/Kg of TA (equimolar to 100 mg/Kg of TN) were administered to the remaining 3 rats, respectively. Each hypotensive agent was orally administered once a day over a period of 4 weeks in the form of a suspension in gum arabic. Gum arabic solution was administered to the Control (non-administered) group. Simultaneously with initiation of the administration, drinking water was exchanged from service water to a 1% aqueous solution of sodium chloride.

In the control (non-administered) group, 3 among 10 rats were dead within 1 week from exchange of drinking water from service water to the sodium chloride solution, and one rat died on the 4th week. In each of these 4 dead cases, the blood pressure was as extremely high as 200 mm Hg or high higher, but neither decrease of the body weight nor other symptoms of asthenia were observed. They died by a slight stress on administration or measurement of the blood pressure. On autopsy, cerebral hemorrhage or other disorder was not observed. Accordingly, it was construed that they died of the heart shock.

No dead case was found in the administered groups. SHR generally likes an aqueous solution of sodium chloride. In the administered groups, after 1 to 2 weeks from the exchange of drinking water, the intake of the aqueous solution of sodium chloride and the amount of urine drastically increased. The change of the blood pressure in old SHR observed when drinking water was exchanged from service water to a 1% aqueous solution of sodium chloride is shown in FIG. 2.

Figure 2:
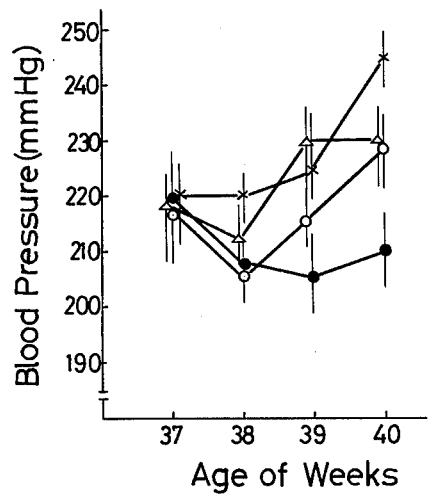
FIG. 2 illustrates the blood pressure values in old SHR.
Figure 3:
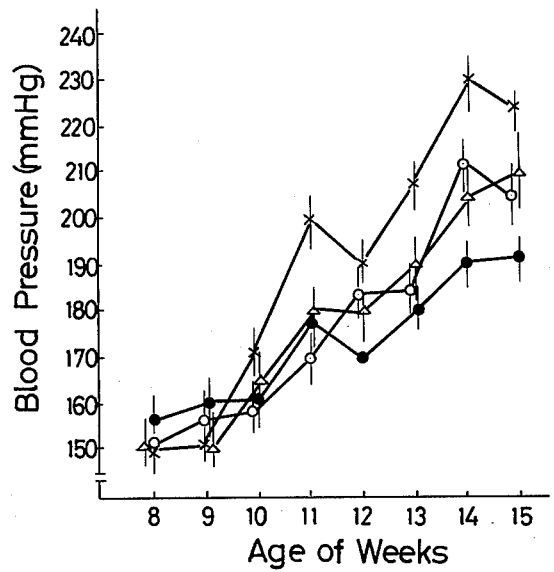
FIG. 3 illustrates the blood pressure values in young SHR.

As is seen from FIG. 2, the blood pressure was lowered by 15 mm Hg on the average after 1 week from the start of administration in the 100 mg/Kg TN administered group and on the 3rd week, there was observed a difference of about 30 mm Hg of the blood pressure between the control group and the 100 mg/Kg TN administered group.

(B) Experiment on Young SHR:

72 of 7-week-old female SHR (having a body weight of 130 to 175 g) were divided into 9 cages, each consisting of 8 rats. Service water was given as drinking water to rats of two cages among these 9 cages, and these rats were compared with other rats which were given a 1% aqueous solution of sodium chloride as drinking water. In each of the 9 cages of rats to which the sodium chloride solution was given, no agent was administered to 2 of 8 rats, 20 mg/Kg of TN was administered to another 2 rats, 100 mg/Kg of TN was administered to still another 2 rats, and 88 mg/Kg of TA was administered to the remaining 2 rats.

After 2 weeks' feeding with the sodium chloride solution, administration was conducted once a day. Within 2 weeks from the start of administration, 3 rats in the Control (non-administered) group, one rat in the 20 mg/Kg TN administered group, 3 rats in the 100 mg/Kg TN administered group, 3 rats in the 88 mg/Kg TA administered group and 4 rats in the service water given group were dead. In view of the body weight decrease and the snivel secretion and from the results of autopsy, it was judged that each of them died of pneumonia. The rats that died prior to initiation of the administration were not taken in account in evaluating the experimental results.

Within 6 weeks from the start of the administration, 5 among 11 rats of the Control (non-administered) group, 3 amoung 13 rats of the 20 mg/Kg TN administered group, 4 among 11 rats of the 100 mg/Kg TN administered group, 3 among 11 rats of the 88 mg/Kg TA administered group and 1 among 12 rats of the service water given group were dead. It was considered that most of the rats dead within 4 weeks from the start of the administration died of pneumonia, but it was considered that most of the rats dead in the latter stage died by shock, namely by exasperation of hypertension.

From the foregoing results of the pharmacological tests made on animals, it will readily be understood that TN and TA have a hypotensive effect.

In order to demonstrate specifically the effects according to the present invention, results of two examples of the clinical experiments conducted according to the double blind test method will now be described.

Clinical Test I (1) Objects:

94 patients of hypertension or arteriosclerosis having subjective symptoms were tested, and some of them suffered from complications such as ischemia heart disease, hypertensive heart disease and encephalomalacia.

(2) Administration Method and Dosage:

As the active drug, there were employed hard capsules, each containing 100 mg of TN. As the control drug, there were employed inactive placebo capsules, which could not be distinguished from the active drug capsules from the appearance.

Two capsules were orally administered at one time, and the administration was conducted three times a day after eating. The period of the administration was principally 4 weeks or 6 weeks. During this period, the administration was performed continuously. Combined administration of drugs having the same function as that of TN (vitamin E drugs, nicotinic acid, its derivatives and peripheral vasolidators) was prohibited. Drugs which had been continuously administered since before the start of the administration of TN were similarly administered according to the disease case and symptom, and change of the prescription during the test was avoided.

(3) Results:

Classification of patients by the sex and age was as shown in Tables 2 and 3, from which it will readily be understood that there was no deviation between the TN administered group and placebo administered group (hereinafter referred to as "P group"). Numbers of patients of arteriosclerosis and hypertension and the maximum and minimum blood pressures were as shown in Tables 4 and 5, from which it will readily be understood that there was no deviation also with respect to these factors. The administration was interrupted in 2 patients in the TN group and in 3 patients in the P group, 5 patients in total. In other 89 patients, the test was completed.

Table 2

| | Classification by Sex | | |
|---|---|---|---|
| | TN Group | P Group | Total |
| Male | 20 patients | 21 patients | 41 patients |
| Female | 24 patients | 24 patients | 48 patients |
| Total | 44 patients | 45 patients | 89 patients |

Table 3

| | Classification by Age | | |
|---|---|---|---|
| Age | TN Group | P Group | Total |
| (43) – 49 | 4 patients | 4 patients | 8 patients |
| 50 – 59 | 13 patients | 12 patients | 25 patients |
| 60 – 69 | 12 patients | 15 patients | 27 patients |
| 70 – 79 | 12 patients | 12 patients | 24 patients |
| 80 –(84) | 3 patients | 2 patients | 5 patients |
| Total | 44 patients | 45 patients | 89 patients |
| Average Age | 63.3 | 63.8 | |
| Standard Deviation | ±10.9 | ±9.5 | |

Table 4

| | Classification by Disease | | |
|---|---|---|---|
| | TN Group | P Group | Total |
| Hypertension and Arteriosclerosis | 23 patients | 21 patients | 44 patients |
| Hypertension | 8 patients | 11 patients | 19 patients |
| Arteriosclerosis | 13 patients | 13 patients | 26 patients |
| Total | 44 patients | 45 patients | 89 patients |

Table 5

| Blood Pressure before Administration | | | |
|---|---|---|---|
| | | TN Group | P Group |
| Maximum | Average Value | 147.6 | 147.0 |

Table 5-continued

| | | Blood Pressure before Administration | |
|---|---|---|---|
| | | TN Group | P Group |
| Pressure (mm Hg) | Standard Deviation | ±23.6 | ±19.7 |
| Minimum Pressure | Average Value | 84.4 | 86.7 |
| (mm Hg) | Standard Deviation | −13.7 | ±14.9 |

With respect to data collected separately in the TN group and the P group, the significant difference was examined according to the statistical method.

(A) Clinical Test Results:

(i) Blood Pressure:

The variation of the blood pressure was as shown in Table 6.

Table 6

| | Variation of Blood Pressure | | | |
|---|---|---|---|---|
| | before administration | 2 weeks | 4 weeks | 6 weeks |
| Maximum Blood Pressure | | | | |
| TN Group | | | | |
| Patient Number | 43 | 34 | 38 | 20 |
| Average Value±S.D. | 147.6±23.6 | 139.7±21.1 | 140.0±20.3 | 138.1±15.2 |
| P Group | | | | |
| Patient Number | 40 | 31 | 30 | 19 |
| Average Value±S.D. | 147.0±19.7 | 144.8±15.5 | 143.3±19.7 | 135.8±21.3 |
| Minimum Blood Pressure | | | | |
| TN Group | | | | |
| Patient Number | 43 | 34 | 38 | 20 |
| Average Value±S.D. | 84.4±13.7 | 82.4±11.4 | 80.6±10.3 | 79.1±7.0 |
| P Group | | | | |
| Patient Number | 40 | 31 | 30 | 19 |
| Average Value±S.D. | 86.7–14.9 | 83.5±11.3 | 83.9±9.9 | 83.0±11.0 | account, in the TN administered group the maximum blood pressure was lowered by 2, 4 or 6 weeks' administration below the maximum blood pressure before the start of the administration.

(B) General Improvement:

The general improvement was evaluated by the attendant physician based on subjective symptoms and test results according to the following scale:

i: remarkable improvement
ii: slight improvement
iii: partial improvement
iv: not changed
v: worsened When 2, 4 or 6 weeks had passed from the start of the administration, the improvement was evaluated based on the symptoms before the administration. Results are shown in Table 8.

Table 7

Variation of Maximum Blood Pressure in Hypertensives (comparison of maximum blood pressure before administration with that 2, 4 or 6 weeks after start of administration in same patients; corresponding to assay)

| | | TN Group | | P Group | |
|---|---|---|---|---|---|
| before administration | Patient Number | 28 | | 27 | |
| | Average Value ± S.D. | 151.0 ± 22.1 | | 151.6 ± 11.2 | |
| | | | $P < 0.05$ | | |
| ↓ 2 weeks | Patient Number | 28 | | 27 | |
| | Average Value ± S.D. | 143.8 ± 21.0 | | 147.7 ± 15.6 | |
| before administration | Patient Number | 29 | | 24 | |
| | Average Value ± S.D. | 154.6 ± 24.8 | | 154.3 ± 16.9 | |
| | | | $P < 0.02$ | | $P < 0.05$ |
| ↓ 4 weeks | Patient Number | 29 | | 24 | |
| | Average Value ± S.D. | 143.1 ± 21.1 | | 141.7 ± 30.7 | |
| before administration | Patient Number | 13 | | 14 | |
| | Average Value ± S.D. | 151.2 ± 28.9 | | 149.1 ± 16.1 | |
| | | | $P < 0.05$ | | |
| ↓ 6 weeks | Patient Number | 13 | | 14 | |
| | Average Value ± S.D. | 139.2 ± 16.8 | | 138.9 ± 24.0 | |

From the results shown in Table 7, it is seen that when only patients of hypertension were taken into Table 8

| | General Improvement Every Two Weeks after Administration | | | | | | |
|---|---|---|---|---|---|---|---|
| | Remarkable Improvement | Slight Improvement | Partial Improvement | Not Changed | Worsened | Total | Improvement Ratio |
| 2 weeks' administration | | | | | | | |
| TN Group | 6 | 9 | 13 | 9 | 1 | 38 | 73.7 % |
| P Group | 4 | 11 | 9 | 11 | 0 | 35 | 68.6 % |
| 4 weeks' administration | | | | | | | |
| TN Group | 6 | 14 | 14 | 5 | 0 | 39 | 87.2 % |
| P Group | 6 | 11 | 5 | 14 | 0 | 36 | 61.1 % |
| | | | | | | | $P = 0.0127$ ⓔ |
| 6 weeks' administration | | | | | | | |
| TN Group | 8 | 5 | 7 | 1 | 0 | 21 | 95.2 % |
| P Group | 4 | 6 | 4 | 7 | 1 | 22 | 63.6 % |

Table 8-continued

| | General Improvement Every Two Weeks after Administration | | | | | | |
|---|---|---|---|---|---|---|---|
| | Remarkable Improvement | Slight Improvement | Partial Improvement | Not Changed | Worsened | Total | Improvement Ratio |
| | | | | | | | P = 0.0094 ⓒ |

ⓒ : according to Fischer direct probability calculation method

As is seen from the results shown in Table 8, in the TN administered group, the improvement ratio was increased every two weeks, while the improvement ratio was hardly changed in the P group. The patients were divided into two groups, namely the improved group and the unchanged or worsened group, and the significant difference assay was conducted between the TN group and the P group. When two weeks had passed from the start of the administration, there was no significant difference between the two groups, but when 4 to 6 weeks had passed from the start of the administration, significantly better results were obtained in the TN group than in the P group.

(C) Improvement Ratios of Respective Subjective Symptoms:

Improvement ratios of respective subjective symptoms were as shown in Table 9.

Table 9

| | Improvement Ratios of Respective Subjective Symptoms | | | | |
|---|---|---|---|---|---|
| Subjective Symptom | Group | Improved | Unchanged or Worsened | Total | Improvement Ratio (%) |
| 1 Headache | TN | 25 | 5 | 30 | 83.3 |
| | P | 22 | 6 | 28 | 78.6 |
| 2 Heaviness in Head | TN | 23 | 5 | 28 | 82.1 |
| | P | 20 | 12 | 32 | 62.5 |
| 3 Virtigo | TN | 6 | 3 | 9 | 66.7 |
| | P | 3 | 5 | 8 | 37.5 |
| 4 Dizzy Feeling | TN | 13 | 3 | 16 | 81.3 |
| | P | 10 | 10 | 20 | 50.0 |
| 5 Syncope | TN | 6 | 2 | 8 | 75.0 |
| | P | 4 | 6 | 10 | 40.0 |
| 6 Tinnitus | TN | 8 | 8 | 16 | 50.0 |
| | P | 10 | 9 | 19 | 52.6 |
| 7 Rush of Blood | TN | 9 | 4 | 13 | 69.2 |
| | P | 5 | 5 | 10 | 50.0 |
| 8 Stiffness in Shoulders | TN | 17 | 9 | 26 | 65.4 |
| | P | 14 | 17 | 31 | 45.2 |
| 9 Stiffness in Nape | TN | 17 | 8 | 25 | 68.0 |
| | P | 14 | 18 | 32 | 43.8 |
| 10 Short Breath | TN | 3 | 4 | 7 | 42.9 |
| | P | 7 | 6 | 13 | 53.8 |
| 11 Oppression on Breast | TN | 5 | 3 | 8 | 62.5 |
| | P | 7 | 4 | 11 | 63.6 |
| 12 Pain on Breast | TN | 5 | 2 | 7 | 71.4 |
| | P | 3 | 0 | 3 | 100.0 |
| 13 Palpitation | TN | 8 | 3 | 11 | 72.7 |
| | P | 10 | 3 | 13 | 76.9 |
| 14 Languor | TN | 9 | 6 | 15 | 60.0 |
| | P | 12 | 5 | 17 | 70.6 |
| 15 Depression | TN | 3 | 4 | 7 | 42.9 |
| | P | 7 | 2 | 9 | 77.8 |
| 16 Irritation | TN | 2 | 1 | 3 | 66.7 |
| | P | 4 | 4 | 8 | 50.0 |
| 17 Insomnia | TN | 15 | 3 | 18 | 83.3 |
| | P | 9 | 10 | 19 | 47.4 |
| 18 Forgetfulness | TN | 7 | 11 | 18 | 38.9 |
| | P | 5 | 18 | 23 | 21.7 |
| 19 Palsy in Limbs | TN | 19 | 4 | 23 | 82.6 |
| | P | 14 | 12 | 26 | 53.8 |
| 20 Chill on Limbs | TN | 5 | 9 | 14 | 35.7 |
| | P | 7 | 10 | 17 | 41.2 |
| 21 Warmness | TN | 7 | 2 | 9 | 77.8 |
| | P | 6 | 3 | 9 | 66.7 |
| 22 Pains on Waist and Back | TN | 11 | 6 | 17 | 64.7 |
| | P | 6 | 9 | 15 | 40.0 |

In the above Table, the "Improved" means that the symptom was improved by at least one grade as compared with the symptom before the administration, and each number denotes the total number of the patients in whom the symptom was thus improved.

It was found that in the TN administered groups, excellent effects were attained for relief of headache, vertigo, dizzy feeling, syncope, stiffness in the shoulders, stiffness in the nape, palsy in limbs, insomnia and pains on the waist and the back. Results are shown in Table 10.

Table 10

| Symptom | Group | Improved by 4 grades | Improved by 3 grades | Improved by 2 grades | Improved by 1 grade | Not Changed | Worsened by 1 grade | Worsened by 2 grades | Total | Improvement ratio (%) | Significant Difference Assay |
|---|---|---|---|---|---|---|---|---|---|---|---|
| Headache | TN | 0 | 4 | 12 | 7 | 4 | 1 | 0 | 28 | 82.1 | $\chi_0^2 = 3.1277*$ |
| | P | 0 | 3 | 8 | 9 | 12 | 0 | 0 | 32 | 62.5 | $P < 0.10$ |
| Vertigo | TN | 1 | 1 | 3 | 1 | 2 | 1 | 0 | 9 | 66.7 | |
| | P | 0 | 1 | 2 | 0 | 5 | 0 | 0 | 8 | 37.5 | |
| Dizzy Feeling | TN | 1 | 1 | 11 | 0 | 2 | 1 | 0 | 16 | 81.3 | $\chi_0^2 = 7.4243*$ |
| | P | 0 | 2 | 4 | 4 | 10 | 0 | 0 | 20 | 50.0 | $P < 0.01$ |
| Vertigo plus Dizzy Feeling | TN | 2 | 2 | 14 | 1 | 4 | 2 | 0 | 25 | 73.1 | $\chi_0^2 = 8.3955*$ |
| | P | 0 | 3 | 6 | 4 | 15 | 0 | 0 | 28 | 46.4 | $P < 0.005$ |
| Stiffness in Shoulders | TN | 2 | 0 | 5 | 10 | 8 | 1 | 0 | 26 | 65.4 | |
| | P | 1 | 1 | 6 | 6 | 17 | 0 | 0 | 31 | 45.2 | |
| Stiffness in Nape | TN | 0 | 1 | 5 | 11 | 5 | 2 | 1 | 25 | 68.0 | $\chi_0^2 = 3.3270$ |
| | P | 1 | 2 | 5 | 6 | 18 | 0 | 0 | 32 | 43.8 | $P < 0.10$ |
| Stiffness in Shoulders and Nape | TN | 2 | 1 | 21 | 13 | 3 | 1 | 0 | 51 | 66.7 | $\chi_0^2 = 5.6104$ |
| | P | 2 | 3 | 11 | 12 | 35 | 0 | 0 | 63 | 44.4 | $P < 0.025$ |

Table 10-continued

| Symptom | Group | Improved by 4 grades | Improved by 3 grades | Improved by 2 grades | Improved by 1 grade | Not Changed | Worsened by 1 grade | Worsened by 2 grades | Total | Improvement ratio (%) | Significant Difference Assay |
|---|---|---|---|---|---|---|---|---|---|---|---|
| Palsy in Limbs | TN | 0 | 1 | 7 | 11 | 4 | 0 | 0 | 23 | 82.6 | P = 0.0318 ⊚ |
|  | P | 0 | 2 | 6 | 6 | 12 | 0 | 0 | 26 | 53.8 |  |
| Insomnia | TN | 1 | 0 | 7 | 7 | 2 | 1 | 0 | 18 | 83.3 | P = 0.0247 ⊚ |
|  | P | 1 | 1 | 5 | 2 | 8 | 2 | 0 | 19 | 47.4 |  |

Notes
*The patients were divided into two groups, one in which the symptom was improved by at least 2 grades (the sum of the patients in which the symptoms were improved by 2, 3 and 4 grades) and the other in which the symptom was improved by one grade, unchanged or worsened. The assay was conducted on these two groups. (In other cases, the patients were divided into two groups, one in which the symptom was improved by one grade and the other in which the symptom was unchanged or worsened, and the assay was made on these two groups.)
⊚ according to Fischer direct probability calculation method.

Results of the clinical experiment conducted according to the double blind method in a different hospital will now be described.

Clinical Experiment II (1) Objects:

75 patients of hypertension or arteriosclerosis having subjective symptoms were tested. Some of them suffered from complications such as ischemia heart disease and cerebral thrombosis. They are detailed in Table 11.

Table 11
Number of Patients Classified by Sex, Age and Disease

|  | TN Group | P Group | Total |
|---|---|---|---|
| Sex | (N=38) | (N=37) |  |
| Male | 16 | 19 | 35 |
| Female | 22 | 18 | 40 |
| Age |  |  |  |
| (33) – 39 | 4 | 5 | 9 |
| 40 – 49 | 9 | 9 | 18 |
| 50 – 59 | 8 | 11 | 19 |
| 60 – 69 | 10 | 5 | 15 |
| 70 – (76) | 7 | 7 | 14 |
| Total | 38 | 37 | 75 |
| Average | 56.45 | 55.27 |  |
| S.D. | ±12.49 | ±11.76 |  |
| Disease |  |  |  |
| Arteriosclerosis | 4 | 2 | 6 |
| Hypertension | 12 | 9 | 21 |
| Arteriosclerosis plus Hypertension | 2 | 3 | 5 |
| Cerebral Arteriosclerosis | 8 | 9 | 17 |
| Cerebral Arteriosclerosis plus Hypertension | 8 | 5 | 13 |
| Ischemia Heart Disease | 2 | 3 | 5 |
| Peripheral Circulatory Trouble | 2 | 6 | 8 |
| Total | 38 | 37 | 75 |

(2) Administration Method and Dosage:

As the active drug, there were employed hard capsules containing 100 mg of TN per capsule, and as the control drug, there were employed inactive placebo capsules, which could not be distinguished from the above capsules of TN from the appearance. Two capsules were administered at one time, and the administration was conducted 3 times per day after eating. The duration of the continuous administration was 4 weeks. Combined use of drugs having the same functions as those of TN (vitamin E drugs, nicotinic acid, its derivatives and peripheral vasolidators) and minor tranquilizers was prohibited.

(3) Experimental Results:

(a) Results of Blood Pressure Test: Variations of the blood pressure in all the patients and in the patients of hypertension alone are shown in Tables 12 and 13.

Table 12
Blood Pressure Values of All Patients

|  |  | Before Administration | After Administration |
|---|---|---|---|
| Maximum Pressure |  |  |  |
| TN Group | N | 38 | 35 |
|  | Average Value | 144.63 | 141.40 |
|  | S.D. | ±25.14 | ±23.65 |
| P Group | N | 36 | 33 |
|  | Average Value | 140.72 | 141.58 |
|  | S.D. | ±19.71 | ±23.85 |
| Minimum Pressure |  |  |  |
| TN Group | N | 38 | 35 |
|  | Average Value | 81.37 | 81.89 |
|  | S.D. | ±14.78 | ±13.64 |
| P Group | N | 36 | 33 |
|  | Average Value | 79.72 | 77.76 |
|  | S.D. | ±11.80 | ±11.39 |

Table 13
Blood Pressure Values of Patients of Hypertension

|  |  | Before Administration | After Administration |
|---|---|---|---|
| Maximum Pressure |  |  |  |
| TN Group | N | 22 | 22 |
|  | Average Value | 160.09 | 148.59 $P < 0.05$ |
|  | S.D. | ±18.88 | ±20.69 |
| P Group | N | 16 | 16 |
|  | Average Value | 153.13 | 155.38 |
|  | S.D. | ±15.46 | ±22.58 |
| Minimum Pressure |  |  |  |
| TN Group | N | 22 | 22 |
|  | Average Value | 89.00 | 87.45 |
|  | S.D. | ±12.74 | ±13.08 |
| P Group | N | 16 | 16 |
|  | Average Value | 83.00 | 83.25 |
|  | S.D. | ±9.35 | ±9.21 |

The change of the blood pressure in the patients of hypertension to whom a hypotensive agent was administrated in combination with TN is shown in Table 14, and the change of the blood pressure in the patients to whom no hypotensive agent was administrated in combination with TN is shown in Table 15.

Table 14
Change of Blood Pressure Value in Patients to Whom Hypotensive Agent was Administered in Combination with TN

|  |  | Before Administration | After Administration |
|---|---|---|---|
| Maximum Pressure |  |  |  |
| TN Group | N | 14 | 14 |
|  | Average Value | 159.29 | 150.00 |
|  | S.D. | ±17.29 | ±21.71 |
| P Group | N | 10 | 10 |
|  | Average Value | 151.00 | 153.20 |
|  | S.D. | ±14.31 | ±9.00 |
| Minimum Pressure |  |  |  |
| TN Group | N | 14 | 14 |
|  | Average Value | 89.71 | 87.43 |
|  | S.D. | ±10.75 | ±13.44 |
| P Group | N | 10 | 10 |
|  | Average Value | 85.40 | 87.20 |

Table 14-continued
Change of Blood Pressure Value in Patients to Whom Hypotensive Agent was Administered in Combination with TN

| | | Before Administration | After Administration |
|---|---|---|---|
| | S.D. | ±11.04 | ±8.21 |

Table 15
Change of Blood Pressure Value in Patients to Whom No Hypotensive Agent was Administered in Combination with TN

| | | Before Administration | After Administration |
|---|---|---|---|
| Maximum Pressure | | | |
| TN Group | N | 8 | 8 |
| | Average Value | 161.50 | 146.13 $P < 0.1$ |
| | S.D. | ±22.60 | ±19.95 |
| P Group | N | 6 | 6 |
| | Average Value | 156.67 | 159.00 |
| | S.D. | ±18.01 | ±36.85 |
| Minimum Pressure | | | |
| TN Group | N | 8 | 8 |
| | Average Value | 87.75 | 87.50 |
| | S.D. | ±16.40 | ±13.34 |
| P Group | N | 6 | 6 |
| | Average Value | 79.00 | 76.67 |
| | S.D. | ±3.52 | ±7.23 |

In each of the foregoing Tables, N indicates the number of the patients, and S.D. denotes the standard deviation.

As is apparent from the results shown in Tables 12 to 15, the hypotensive effect was attained in the TN administrated group as compared with the P group. Especially in the case of patients of hypertension alone, significant lowering of the blood pressure was observed at a level of significance lower than 5%.

(b) Liver Function Test Results:

Liver function test results are shown in Table 16, from which it will readily be understood that in each of GOT, GPT, LDH and ALP, the variation was within the normal region. The tendency of reduction of GOT and GPT was greater in the TN administered group than in the P group.

Table 16
Liver Function Test Results

| | | | Before Administration | After Administration |
|---|---|---|---|---|
| GOT | TN Group | N | 37 | 29 |
| | | Average Value | 28.59 | 24.90 |
| | | S.D. | ±14.92 | ±9.51 |
| | P Group | N | 35 | 32 |
| | | Average Value | 28.29 | 35.13 |
| | | S.D. | ±26.75 | ±57.51 |
| GPT | TN Group | N | 37 | 30 |
| | | Average Value | 22.73 | 18.73 |
| | | S.D. | ±19.46 | ±13.40 |
| | P Group | N | 36 | 33 |
| | | Average Value | 21.94 | 23.67 |
| | | S.D. | ±14.67 | ±25.37 |
| LDH | TN Group | N | 36 | 30 |
| | | Average Value | 251.28 | 245.03 |
| | | S.D. | ±72.42 | ±53.94 |
| | P Group | N | 34 | 33 |
| | | Average Value | 244.26 | 250.58 |
| | | S.D. | ±75.10 | ±56.54 |
| ALP | TN Group | N | 34 | 30 |
| | | Average Value | 7.37 | 7.21 |
| | | S.D. | ±2.36 | ±2.21 |
| | P Group | N | 34 | 30 |
| | | Average Value | 7.27 | 7.29 |
| | | S.D. | ±2.51 | ±2.57 |

(c) Kidney Function Test Results:

The kidney function test results are shown in Table 17, from which it will readily be understood that the variation of BUN values was within the normal region.

Table 17
Kidney Function Test Results

| | | | Before Administration | After Administration |
|---|---|---|---|---|
| BUN | TN Group | N | 31 | 27 |
| | | Average Value | 14.74 | 14.99 |
| | | S.D. | ±6.23 | ±8.48 |
| | P Group | N | 32 | 28 |
| | | Average Value | 13.26 | 13.44 |
| | | S.D. | ±3.52 | ±3.72 |

(d) Urine Test Results:

The results are shown in Table 18.

Table 18
Urine Test Results

| | | | Before Administration | After Administration |
|---|---|---|---|---|
| specific Gravity | TN Group | N | 25 | 25 |
| | | Average Value | 1017.56 | 1017.92 |
| | | S.D. | ±5.56 | ±5.34 |
| | P Group | N | 24 | 24 |
| | | Average Value | 1015.79 | 1018.25 |
| | | S.D. | ±6.04 | ±5.30 |

(e) Urine Sugar, Urine Protein and Urobinogen Test Results:

The results are shown in Table 19 to 21.

Table 19
Sugar in Urine

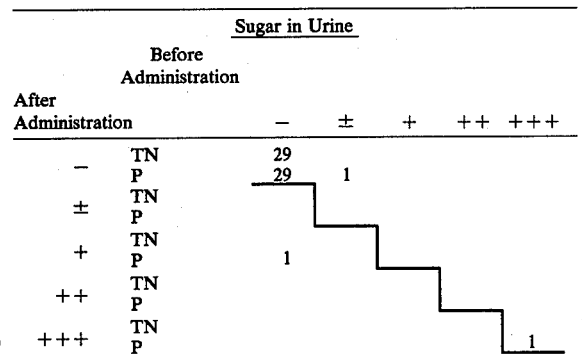

Table 20
Protein in Urine

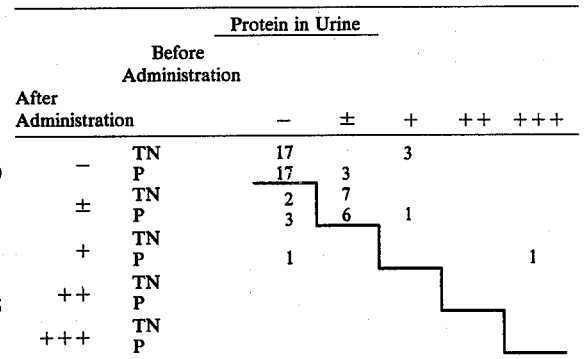

Table 21

| After Administration | Before Administration Urobilinogen | | | | |
|---|---|---|---|---|---|
| | | − | ± | + | ++ | +++ |
| − | TN | 14 | | | | |
| | P | 12 | 1 | | | |
| ± | TN | | 11 | 1 | | |
| | P | | 10 | 1 | | |
| + | TN | | | 2 | | |
| | P | | 1 | 3 | 1 | |
| ++ | TN | | | | | |
| | P | | | | | |
| +++ | TN | | | | | |
| | P | | | | | |

None of results of other various blood tests and the like were suggestive of undesirable, side effects by administration of TN.

(f) Improvement of Subjective Symptoms:

Changes of various subjective symptoms of patients of hypertension were collectively examined, and at the time of termination of the administration, the degrees of improvements were judged and evaluated in both the TN administered group and the P group, to obtain results shown in Table 22.

Table 22

| Degree of Improvement of Subjective Symptoms | | |
|---|---|---|
| | TN Group | P Group |
| Remarkable Improvement | 7 | 2 |
| Slight Improvement | 6 | 6 |
| Partial Improvement | 6 | 1 |
| Not Changed | 3 | 8 |
| Worsened | 0 | 0 |
| Total | 22 | 17 |
| Improvement Ratio (%) | 86.36 | 52.94 |
| | $P < 0.05$ | |

From the above results, it is seen that the degree of the improvement in the TN administered group was excellent over that in the P group at a level of significance lower than 5%.

(g) General Improvement:

With respect to patients of hypertension alone, the general improvement was evaluated collectively based on subjective symptoms and clinical test data to obtain results shown in Table 23.

Table 23

| General Improvement | | |
|---|---|---|
| | TN Group | P Group |
| Remarkable Improvement | 4 | 1 |
| Slight Improvement | 8 | 5 |
| Partial Improvement | 7 | 3 |
| Not Changed | 3 | 8 |
| Worsened | 0 | 0 |
| Total | 22 | 17 |
| Improvement Ratio (%) | 86.36 | 52.94 |
| | $P < 0.05$ | |

From the above results, it is seen that the improvement in the TN administered group was excellent over that in the P group at a level of significance lower than 5%.

(h) Side Effects:

Among 41 patients of the TN administered group, one complained of light lack of appetite and another patient complained of constipation. In other patients, no side effect was observed.

From the results of the above two clinical experiments, the following can be concluded.

(1) The hypotensive effect on the patients of hypertension was higher in the TN administered group than in the P group.

(2) The general improvement in the TN administered group was significantly excellent over that in the P group at a level of significance lower than 0.5%.

(3) The degree of the improvement of subjective symptoms in the TN administered group was higher than in the P group. The administration of TN manifested especially good effects for improving rush of blood, dizzy feeling stiffness in the shoulders, stiffness in the nape, heaviness in the head and insomnia.

(4) Side effects were much more reduced in TN than in conventional hypotensive agents.

Thus, it was confirmed that TN is a very effective and safe hypotensive agent.

TN is distinguished from conventional hypotensive agents in the point that the effect is manifested relatively moderately but occurrence of side effects can be much reduced. Further, TN shows a high effect durability. Accordingly, it can be administered continuously for a long time.

Pharmaceutical preparations useful for administration of the active compounds of the present invention will now be described.

Example 1 (Capsules)

| Ingredient | mg in one capsule |
|---|---|
| dl-α-Tocopheryl nicotinate | 100.0 |
| Silicic anhydride | 91.0 |
| Cellulsoe acetate phthalate | 9.0 |

The above ingredients were uniformly mixed, and the homogeneous mixture was filled in gelatin hard capsules.

Example 2 (Tablets)

| Ingredient | Amount (mg) |
|---|---|
| dl-α-tocopheryl nicotinate | 105.0 |
| anhydrous silicic acid hydrate | 30.0 |
| silicic anhydride | 17.0 |
| corn starch | 12.0 |
| refined sugar | 20.0 |
| potassium carboxymethyl cellulose | 10.0 |
| crystalline cellulose (Avicel) | 41.0 |
| polyvinylpyrrolidone (K-30) | 5.0 |
| talc | 10.0 |

In acetone was dissolved d*l*-α-tocopheryl nicotinate, and the solution was absorbed on anhydrous silicic acid hydrate, silicic anhydride and corn starch and then dried. Then, refined sugar, potassium carboxymethyl cellulose and crystalline cellulose were incorporated, and an aqueous solution of PVP (K-30) as the binder was added to the mixture and granules were prepared according to a customary granulation method. Talc was added as the lubricant to the granules and the granules were formed into tablets, each containing 250 mg of the active ingredient.

Example 3 (Enteric Coating Tablets)

Coatings were formed on the surfaces of tablets prepared according to the method described in Example 2, by using a solution of cellulose acetate phthalate in acetone.

Example 4 (Injection Solution)

| Ingredient | Amount (mg) |
| --- | --- |
| dl-α-tocopheryl nicotinate | 100 |
| sorbitol monostearate (Aracel 60) | 40 |
| benzyl alcohol | 40 |
| hydrogenated castor oil-polyoxyethylene 60-mole ether (HCO-60) | 140 |
| sodium hydroxide | 0.12 |
| total | 2 ml | d*l*-α-Tocopheryl nicotinate, Aracel 60, HCO-60 and a part of distilled water for injection were admixed, and benzyl alcohol, sodium hydroxide and the remainder of distilled water for injection were added. The solution was filtered and filled in ampoules having a capacity of 2 ml. The ampoules were melt-sealed and sterilized.

Example 5 (Powder)

| Ingredient | Amount (mg) |
| --- | --- |
| dl-α-tocopheryl nicotinate | 200 |
| microcrystalline cellulose (Avicel) | 380 |
| hydroxypropyl cellulose | 100 |
| silicic anhydride | 200 |
| starch | 120 |
| total | 1000 | d*l*-α-Tocopheryl nicotinate was dissolved in acetone, and the solution was adsorbed on silicic anhydride and starch and then dried. The mixture was combined with other ingredients and the admixture was formed into powder according to a customary method.

Example 6 (Capsules)

| Ingredient | mg in one capsule |
| --- | --- |
| dl-α-tocopheryl acetate | 100.0 |
| silicic anhydride | 92.0 |
| cellulose acetate phthalate | 8.0 |

The foregoing ingredients were uniformly mixed, and homogeneous mixture was filled in gelatin hard capsules.

Example 7 (Tablets)

| Ingredient | Amount (mg) |
| --- | --- |
| dl-α-tocopheryl acetate | 105.0 |
| silicic anhydride | 50.0 |
| corn starch | 10.0 |
| refined sugar | 20.0 |
| potassium carboxymethyl cellulose | 10.0 |
| crystalline cellulose (Avicel) | 40.0 |
| polyvinylpyrrolidone (K-30) | 5.0 |
| talc | 10.0 |

In the same manner as described in Example 2, these ingredients were formed into tablets, each containing 250 mg of the active ingredient, according to the customary method.

The embodiments of the invention in which an exclusive property or privilege is claimed are defined as follows:

1. A method of treating hypertension which comprises orally or parenterally administering to a hypertensive subject requiring such treatment, a therapeutically effective amount of d*l*-α-tocopheryl nicotinate, in combination with a pharmceutically acceptable carrier.

2. A method according to claim 1 in which the amount of said d*l*-α-tocopheryl nicotinate administered is from 50 to 120 mg/day.

3. A method according to claim 2 in which said d*l*-α-tocopheryl nicotinate is orally administered.

4. A method according to claim 2 in which said d*l*-α-tocopheryl nicotinate is parenterally administered.

5. A method according to claim 3 in which said hypertensive subject is a human being.

* * * * *

UNITED STATES PATENT AND TRADEMARK OFFICE
CERTIFICATE OF CORRECTION

PATENT NO. : 4 088 778
DATED : May 9, 1978
INVENTOR(S) : Toshiji Igarashi et al

It is certified that error appears in the above-identified patent and that said Letters Patent are hereby corrected as shown below:

Column 18, line 34; change "120 mg/day" to ---1200 mg/day---.

Signed and Sealed this

Seventeenth Day of October 1978

[SEAL]

Attest:

RUTH C. MASON
Attesting Officer

DONALD W. BANNER
Commissioner of Patents and Trademarks